United States Patent
Niebler et al.

(10) Patent No.: US 9,642,584 B2
(45) Date of Patent: May 9, 2017

(54) METHOD FOR CONTROLLING THE MOVEMENT OF AN X-RAY APPARATUS AND X-RAY SYSTEM

(71) Applicant: SIEMENS AKTIENGESELLSCHAFT, Munich (DE)

(72) Inventors: Christine Niebler, Rueckersdorf (DE); Stefan Sattler, Forchheim (DE); Stefan Schuster, Forchheim (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 263 days.

(21) Appl. No.: 13/630,055

(22) Filed: Sep. 28, 2012

(65) Prior Publication Data

US 2013/0083894 A1   Apr. 4, 2013

(30) Foreign Application Priority Data

Sep. 30, 2011   (DE) .................. 10 2011 083 876

(51) Int. Cl.
*A61B 6/00*   (2006.01)
*A61B 6/04*   (2006.01)

(52) U.S. Cl.
CPC .......... *A61B 6/4441* (2013.01); *A61B 6/4458* (2013.01); *A61B 6/4476* (2013.01);
(Continued)

(58) Field of Classification Search
CPC .. A61B 6/03; A61B 6/032; A61B 6/12; A61B 6/481; A61B 6/542; A61B 6/547;
(Continued)

(56) References Cited

U.S. PATENT DOCUMENTS 5,285,772 A * 2/1994 Rattner ............................. 601/4
5,485,502 A * 1/1996 Hinton et al. ................ 378/117
(Continued)

FOREIGN PATENT DOCUMENTS

CN   1488317 A   4/2004
DE   69214490 T2   4/1997
(Continued)

OTHER PUBLICATIONS

Besl et al., A method for Registration of 3D shapes, Feb. 1992, IEEE Transactions on Pattern Analysis and Machine Intelligence, vol. 14, No. 2, p. 244.*

*Primary Examiner* — Glen Kao

(57) ABSTRACT

A method for controlling a movement of an x-ray apparatus is provided. The x-ray apparatus has a C-arm with an x-ray source and an x-ray detector disposed opposite one another, an actuator for positioning the C-arm relative to an examination region of an examination object supported on a support facility, a control facility for controlling the x-ray source and the x-ray detector and the actuator, and an operating facility with a display apparatus and an operating unit. The display apparatus displays an image representing a part of the examination object and a target location of the C-arm being determined as a function of an input at the operating unit. The target location has a target position and a target alignment of the C-arm. A controlled variable of the actuator is determined and supplied to the control facility for controlling the actuator.

19 Claims, 5 Drawing Sheets

(52) U.S. Cl.
CPC ............ *A61B 6/547* (2013.01); *A61B 6/0407* (2013.01); *A61B 6/4464* (2013.01)

(58) Field of Classification Search
CPC ... A61B 6/4441; A61B 6/4405; A61B 6/0407; A61B 6/4458; A61B 6/4464; A61B 6/4476; G01N 23/04
USPC ...... 378/4, 8, 16, 20, 62, 64, 65, 68, 69, 95, 378/98, 98.8, 108, 117, 165, 167, 193, 378/195, 198, 205
See application file for complete search history.

(56) References Cited

U.S. PATENT DOCUMENTS

| | | | |
|---|---|---|---|
| 7,668,290 B2* | 2/2010 | Tanaka | 378/62 |
| 2004/0114706 A1* | 6/2004 | Ikeda et al. | 378/4 |
| 2006/0173273 A1* | 8/2006 | Boese et al. | 600/407 |
| 2007/0244386 A1* | 10/2007 | Steckner | A61B 17/2256 600/411 |
| 2008/0031413 A1* | 2/2008 | Bouvier et al. | 378/63 |
| 2009/0022275 A1* | 1/2009 | Grebner et al. | 378/95 |
| 2009/0086927 A1* | 4/2009 | Wang et al. | 378/206 |
| 2009/0274271 A1* | 11/2009 | Pfister et al. | 378/62 |

FOREIGN PATENT DOCUMENTS

| | | |
|---|---|---|
| DE | 10118183 A1 | 11/2002 |
| DE | 4423359 84 | 10/2005 |
| DE | 102005028215 A1 | 12/2006 |
| DE | 102008046346 A1 | 3/2010 |
| DE | 102009004766 A1 | 7/2010 |

* cited by examiner

METHOD FOR CONTROLLING THE MOVEMENT OF AN X-RAY APPARATUS AND X-RAY SYSTEM

CROSS REFERENCE TO RELATED APPLICATIONS

This application claims priority of German application No. 10 2011 083 876.7 filed Sep. 30, 2011, which is incorporated by reference herein in its entirety.

FIELD OF INVENTION

The present application relates to a method for controlling the movement of an x-ray apparatus. The present application also relates to an x-ray system.

BACKGROUND OF INVENTION

Many medical diagnosis and intervention systems for angiography, cardiology and neurology currently use x-ray devices or x-ray apparatuses as a basis for imaging. The x-ray devices are frequently fitted with a so-called C-arm. A C-arm generally comprises an x-ray source and, on the opposite side of a C-shaped, generally metal connecting support, an x-ray detector. The C-arm can be mounted for example on a so-called gantry, on the ceiling or on a robot-like apparatus. A number of movement axes and adjustment options, which can also be motor-driven, allow flexible positioning of the x-ray source and x-ray detector relative to an examination object, for example a human or animal patient, lying on an examination table or patient couch. The positioning of the C-arm and the components positioned thereon is also referred to as C-arm travel. Recording methods, in which the C-arm is moved rotationally about an examination region, also referred to as a region of interest, ROI, while a larger number of x-ray images are recorded, are becoming increasingly important. Mathematical algorithms are used to reconstruct these so-called rotational x-ray images to form a 3D image dataset.

One problem for the user of such a system, for example physician or a medical assistant, is its not inconsiderable operational complexity. Generally desired travel of the x-ray device and of the C-arm is indicated using joysticks, rocker-type switches or similar operating elements. Depending on the type of system, for example depending on its mechanical structure, the number of degrees of freedom, etc., a number of joysticks and/or multiple functions may be required in order to be able to execute all the possible and necessary movements. Thus for example in the case of a robot-based C-arm gantry it may be necessary to activate six degrees of freedom separately for the gantry alone, specifically three linear movement directions, e.g. the x, y and z directions, and three orientation angles of the C-arm, LAO/RAO, cranial/caudal and the C-arm swivel. Fast and error-free operation is only possible in such instances with a great deal of experience and requires a high level of concentration on operation, not least to avoid spatial collisions. Also with manual operation a position can generally only be reached after successive movements, as only one of the six degrees of freedom can be activated manually in each instance. This takes time and makes intuitive operation in the defined environment problematic. It should also be taken into consideration that in practice the pre-positioning of the x-ray device is often performed during irradiation, increasing radiation exposure and the associated risk of incorrect operation, for example if the C-arm is moved in the wrong direction. This could result in delayed treatment, unintentional collision with objects or personnel or an unnecessary application of x-ray radiation.

Until now the C-arm position and alignment have been controlled by operating modules, generally designed as joysticks and/or buttons, in other words control is effected by electromechanical switching elements, e.g. potentiometers. With these the user moves the joysticks, which are generally mounted permanently on the x-ray apparatus or installed on a trolley or in the examination room, mechanically, thereby closing contacts or changing potentiometer/sensor positions, which are evaluated and converted to a corresponding device movement. There are also fixed operating switches with limited possibility of movement, which are integrated on the flat panel detector. Levers and handles are also standard components of C-arm systems, which are characterized by a smooth-running mechanical system with weight compensation, but these are often only intended to extricate patients in the event of system failure. Travel to another system position, defined by the C-arm position and a correlated examination table position, can also be effected by way of system or so-called user positions. This are either preset, in the case of a system position for example the so-called patient transfer position or the so-called headside position, or can be programmed as so-called user positions by the user, with the Cartesian coordinates of the C-arm position and the associated orientation angles, such as cranial/caudal (CRAN/CAUD), right anterior oblique/left anterior oblique (LAO/RAO), relative to the examination table, being included in the programming. The patient position or the location of the region to be examined, e.g. a specific organ, is not taken into consideration. A user position only allows approximate pre-positioning, if the operator has programmed the user position based on a different patient. The fact that patients are different sizes and can assume different positions on the examination table unit that the use of such user positions is restricted and, from what is said, they are rarely used in practice and only for approximate pre-positioning.

DE 10 2009 004 766 A1 discloses an x-ray facility, the component parts of which are set with the aid of a miniature model of the x-ray facility, with manipulations of a model component part being transferred to a setting of the corresponding component part of the x-ray facility. One disadvantage of this facility is that although operation can be intuitive, positioning is still a function of the individuality of the patient.

SUMMARY OF INVENTION

The object of the present application is to specify a method for controlling the movement of an x-ray apparatus, which allows fast and intuitive positioning of the x-ray apparatus. The intention is also to specify an x-ray system, with which it is possible to perform such a method for controlling the movement of an x-ray apparatus.

The application achieves this object with a method for controlling the movement of an x-ray apparatus with the features of the first independent claim and an x-ray system with the features of the second independent claim.

The basic concept of the application is a method for controlling the movement of an x-ray apparatus, wherein the x-ray apparatus has a C-arm, on which an x-ray source and an x-ray detector can be disposed opposite one another, at least one actuator for positioning the C-arm relative to an examination region of an examination object, which can be supported on a support facility, a control facility for controlling the x-ray source and the x-ray detector and the at least one actuator and an operating facility, comprising a display apparatus and at least one operating unit, the display apparatus of the operating facility displaying an image that represents at least one part of the examination object, and at least one target location of the C-arm being determined as a function of at least one input at the operating unit of the operating facility, the target location comprising a target position and a target alignment of the C-arm, at least one controlled variable of the at least one actuator for positioning the C-arm being determined and the at least one controlled variable of the control facility being supplied to the control facility for controlling the at least one actuator.

The disclosed method is based on an x-ray apparatus with a C-arm. An x-ray source and an x-ray detector can be disposed opposite one another on the C-arm. At least one actuator can be controlled by a control facility to move the C-arm to a desired position, the desired position relating to an examination region of an examination object, e.g. a human or animal patient supported on a support facility, e.g. an examination table or patient couch. An examination region can refer for example to an organ or body region which is to be examined or treated. The control facility can be for example an electronic unit, e.g. a computer, which, also being an integral component of the x-ray apparatus, can control the at least one actuator, as well as the x-ray source and the x-ray detector, and can favorably also receive images from the x-ray detector. The x-ray apparatus also has an operating facility, which comprises a display apparatus, e.g. a monitor or display, and at least one operating unit, e.g. a computer mouse. According to the application the display apparatus of the operating facility displays an image that represents at least one part of the examination object. The at least one part of the examination object displayed in the image comprises the examination region. Represent here means that the image shows the part of the examination object in such a manner that an operator of the x-ray apparatus is able to assign components of the image to the examination object and to an examination region. The displayed part of the examination object is not necessarily as realistic as possible but instead tends to simplify and abstract. By displaying the simple outline of a person viewed from above, it is possible easily to identify for example body regions such as the head, the two feet, the two elbows, etc. According to the application at least one target location of the C-arm, which comprises at least one target position and a target alignment of the C-arm, can be determined by one or more inputs at the operating unit. The arrangement of x-ray source and x-ray detector on the C-arm unit that the position and alignment of the x-ray source and x-ray detector are also defined by the target location of the C-arm. Inputting is favorably effected taking into account the image displayed on the display apparatus of the operating facility. This means that an operator of the x-ray apparatus for example can perform an input at the operating unit of the operating facility by for example clicking with a computer mouse on a point of the image displayed on the display apparatus of the operating facility. It is possible to determine one or more target locations of the C-arm taking into account this input point, for example by a table of assignments of input points and target locations. Also at least one controlled variable of the at least one actuator for positioning the C-arm can be determined from the one or more target locations. The at least one controlled variable can then be supplied to the control facility for controlling the at least one actuator.

Finally the supplied controlled variable can be used to help move the C-arm to the target location by activating the at least one actuator.

The image representing at least one part of the examination object is included in the determination of the target location of the C-arm. It is conceivable here for positions of the image displayed on the display apparatus of the operating facility to be assigned to target locations of the C-arm.

In one development the location of at least one organ and/or the location of at least one body region is marked in the anatomically correct position in the image and the marking of the at least one organ and/or the marking of the at least one body region can be selected by the operating unit. One or more organs, e.g. the lung, heart, kidneys, stomach, intestine, etc., and/or one or more body regions, e.g. the head, lower arms, upper arms, legs, etc., are to be marked in the image that represents at least one part of the examination object. This can be done for example using circles or ellipses. The marking are also to be displayed in the anatomically correct position in the image and can be selected by an operator for example using the operating unit of the operating facility. This represents a very intuitive input option for a target location for the C-arm of the x-ray apparatus.

In a further embodiment the determination of the target location of the C-arm includes at least one statistic for dimensions and/or size ratios of the at least one part of the examination object from a number of examination objects and/or a standard position of the examination region of the examination object relative to the support facility and/or further information about the examination object, such as information from a medical file. At least one statistic for dimensions and/or size ratios of the at least one part of the examination object from a number of examination objects is taken into account here on the image after inputting to determine the target position of the C-arm, in other words positions of the image, which are displayed for example on the display apparatus of the operating facility, are allocated to target locations of the C-arm, which are likely to correspond closely to the actual positions of the examination region of the examination object. It also helps here if standard positions of the examination region of the examination object relative to the support facility are taken into account. This means that for recordings of the head, the head of a patient assumes a location, i.e. a standard position, in relation to the support facility, e.g. the examination table. An even more precise determination of the target location is possible, if additional information relating to the examination object is included in the determination, for example the height or weight of a patient. The target locations of organs and/or body regions can be estimated very precisely with the aid of statistics, for example a statistic in which the location of the stomach was examined as a function of the height of a patient.

In a further embodiment a measurement using a measuring unit of at least one part of the examination object is included in the determination of the target location of the C-arm, the measuring unit comprising one or more measuring unit from the group of cameras in the visible wavelength range, IR cameras, time of flight cameras, laser scanners, pressure-sensitive measuring unit, measuring unit using an inductive measuring effect, measuring unit using a capacitive measuring effect, measuring unit using heat radiation detection, measuring unit comprising a near field antenna. To assign a point selected using the operating part of the operating unit to a target location of the C-arm, it is helpful to determine the actual circumstances of the examination object, for example the actual size and/or the actual position or orientation of the examination object on the support facility. If a patient is not lying in the standard position for example, the assumption that said patient was lying in the standard position would produce incorrect target locations. A very wide range of measuring unit can be used for a measurement. Cameras in the visible wavelength range are widely used and can also allow a spatial image representation, for example by stereoscopic recordings. Cameras with a sensitive image recorder in the infrared (IR) wavelength range have the feature that an examination object covered by sheets can also be recorded. So-called time of flight cameras (TOF) refer to 3D camera systems, which measure distances using a transit time method. The principle is similar to that of laser scanners but here a measuring process captures a matrix of distances. A pressure-sensitive measuring unit can refer for example to a mat with pressure-sensitive sensors. When a patient is positioned on such a mat, it is possible to conclude for example the height, location and also the weight of the patient from the pattern of measurement values. Other measuring unit are based on measurement principles such as induction change, capacity change or heat radiation detection.

In one embodiment of a basic concept of the application an image of at least one part of the examination object recorded with the aid of the x-ray apparatus is included in the determination of the target location of the C-arm. In practice a number of x-ray images are often recorded during an examination. If there is already a first image of at least one part of the examination object recorded with the aid of the x-ray apparatus, this can be used to determine the target location more precisely during the recording of a subsequent image, even if the image detail is to be changed. To this end the location of the C-arm during the recording of the first image can be taken into account if the position of the patient does not change for example. It is conceivable for the recorded image to be segmented using a segmentation algorithm known from the prior art, allowing for example the location of organs to be determined and the target location to be determined taking into account the location of the segmented objects that is now known. It is further conceivable, instead of an image recorded with the aid of the x-ray apparatus, to use one or more images from other imaging procedures, for example CT, MR, ultrasound, which can be registered in the x-ray system in order to be used for example to determine the target location more precisely when recording a subsequent image.

After an input using the at least one operating unit a detail of the image is shown enlarged and/or after an input using the at least one operating unit another representation, such as a different hierarchy of the image, is displayed. For more precise inputting of an operator input using the operating unit of the operating facility the image can be shown enlarged in that for example a region is selected first, which is then enlarged over the entire area of the display apparatus. A different representation, for example a switch from a symbolic representation to a more objective representation, can also help to allow a more precise input. Further the switch from a representation showing the surface of an examination object to a representation reproducing the blood vessels and/or the bone structure can be helpful for intuitive user inputting.

The operating facility comprises a touch-sensitive screen and/or a screen with an input unit, such as a computer mouse, and inputting involves the selection of a point or region on the screen. One input unit that is simple to understand is a touch-sensitive screen or touchscreen, as it can display the image with any markings and can also allow inputting directly by touching the image or markings. The combination of screen or monitor and an input unit, e.g. a computer mouse or joystick, is a further widely used option for actuating an input. All the input methods described can be used to select points or even regions, e.g. to enlarge a detail.

In one development the determination of the at least one controlled variable of the at least one actuator for positioning the C-arm includes an algorithm for optimizing the controlled variable, the optimization relating to a minimization of the positioning time of the of the C-arm. As described in the introduction, x-ray apparatuses are often equipped with a number of movement axes and adjustment options so that the travel of a C-arm to a target location can be time-consuming, for example if a number of individual movements are executed in series, and the process can become very complex. Frequently there is also more than one option for moving the C-arm to a target location, so a great deal of experience is required on the part of the operator, to move the C-arm in an effective manner. To resolve this problem it is proposed that an algorithm should be used, which optimizes the controlled variables for activating the actuator(s) so that the positioning time for the C-arm is minimized. The result could be a sequence of controlled variables for a number of actuators, which are supplied to the control facility and used to activate the actuators in a parallel and optimal manner, so that the time taken to move the C-arm to the target location is minimal. Algorithms for optimizing movement of apparatuses with multiple axes are known from the prior art, such as from the field of robotics, e.g. by the name path planners.

In a further embodiment the determination of the at least one controlled variable of the at least one actuator for positioning the C-arm includes a collision avoidance algorithm, which takes into account the location of the operating facility, the support facility and the examination object. As the C-arm travels, there is a risk of the C-arm colliding with objects in the environment of the x-ray apparatus. To avoid this, it is proposed that an algorithm be used, which changes or optimizes the controlled variables for activating the actuator(s) so that C-arm travel does not result in collision or increased proximity. Objects, the location and extension of which have to be taken into account, are for example the operating facility, the support facility and the examination object. The position and extension of the objects can be stored in a file or are captured with the aid of measuring unit, for example cameras. When cameras are used with image recording frequencies of for example five images per second or more, moving objects such as operating personnel can also be taken into account. Collision avoidance algorithms are known from the prior art, such as from the field of robotics. Examples are also to be found in DE 10 2005 028 215 A1, in which magnetic position sensors are used, or DE 10 2008 046 346 A1, which describes the use of different measuring unit, such as pivotable laser scanners.

In a further embodiment at least one parameter for recording an x-ray image using the x-ray apparatus, such as an exposure time, an image repetition rate, a beam intensity, an x-ray source/detector distance and/or a collimator setting, is determined as a function of the input at the operating unit of the operating facility and supplied to the control facility. In addition to the target location of the C-arm, other parameters that have to be selected to record an x-ray image using the x-ray apparatus can also be determined as a function of the input using the operating unit of the operating facility and supplied to the control facility. This means for example that by selecting a target location, e.g. selecting the left ankle, parameters can be set for recording the x-ray image, e.g. an exposure time of 10 ms. Different settings apply for other regions or organs and these can be stored for example in a file that can be accessed by the control facility. Specific parameter sets for defined examination regions can also be referred to as organ programs.

In a further embodiment a sequence of target locations of the C-arm and/or a sequence of parameter settings for recording an x-ray image using the x-ray apparatus is/are determined as a function of the input at the operating unit of the operating facility. In this embodiment for example a sequence of target locations of the C-arm can be selected as a function of the input using the operating unit of the operating facility. For example when selecting the right leg and in some instances making an additional input using the operating unit of the operating facility, the C-arm is moved in such a manner that digital subtraction angiography, DSA, can be performed.

The method is expediently executed in a repeated manner until a termination criterion, such as reaching of a predefinable number of method runs or the completion of a predefinable time period or the actuation of a button or the actuation of a switch, is met. In other words the method is terminated when a termination criterion is met.

It is favorable for the method to be executed automatically. The execution of the method only requires one input at the operating unit of the operating facility and all the further method steps are performed automatically.

A further basic concept of the application relates to an x-ray system, comprising an x-ray apparatus, the x-ray apparatus having a C-arm, on which an x-ray source and an x-ray detector can be disposed opposite one another, at least one actuator for positioning the C-arm relative to an examination region of an examination object which can be supported on a support facility, a control facility for controlling the x-ray apparatus and the at least one actuator and an operating facility, comprising a display apparatus and at least one operating unit. The display apparatus of the operating facility is embodied to display an image that represents at least one part of the examination object and to determine at least one target location of the C-arm as a function of at least one input at the operating unit of the operating facility, the target location comprising a target position and a target alignment of the C-arm, to determine at least one controlled variable of the at least one actuator for positioning the C-arm and to supply the at least one controlled variable to the control facility for controlling the at least one actuator.

In a further embodiment the x-ray system is embodied to execute a method as described above. An x-ray system has unit, e.g. electronic processors or input unit, such as touch-sensitive displays, or measuring unit, such as cameras etc., which are able to execute a method as described above.

BRIEF DESCRIPTION OF THE DRAWINGS

The embodiments described in more detail below represent embodiments of the present application. Further developments will emerge from the figures and description below.

DETAILED DESCRIPTION OF INVENTION

Figure 1:
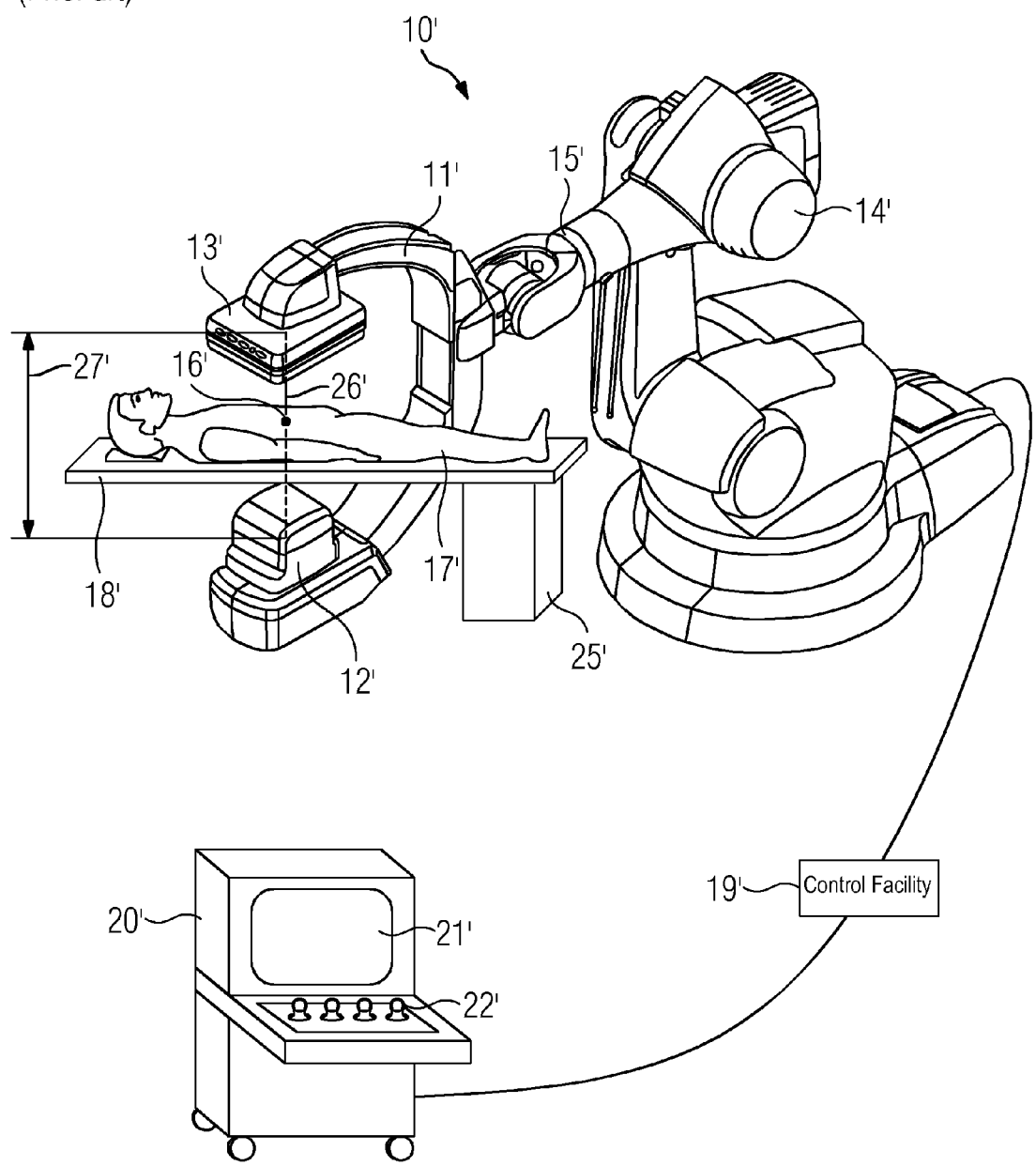
FIG. 1 shows an x-ray apparatus according to the prior art.

FIG. 1 shows an x-ray apparatus 10' according to the prior art. The x-ray apparatus 10' has a C-arm 11', on which an x-ray source 12' and an x-ray detector 13' are disposed opposite one another. Lying on a support facility 18', e.g. an examination table, which is held in a movable manner by a column of the support facility 25', is an examination object 17', in this instance a person. The x-ray apparatus 10' is controlled by an operating facility 20', which comprises a number of operating unit 22', in this instance joysticks, and a display apparatus 21', in this instance a monitor, and a control facility 19'. The control facility 19' forwards inter alia controlled variables or control signals to actuators (the actuators 14' and 15' are shown by way of example) to the x-ray apparatus 10'. The C-arm 11' of the x-ray apparatus 10' is disposed on a robot-like apparatus, which allows a number of degrees of freedom for the positioning and alignment of the C-arm 11' and thus of the x-ray source 12' and x-ray detector 13'. A target location of the C-arm 11', or of the x-ray source 12' and x-ray detector 13', is assumed in FIG. 1, so that the central beam 26' of the x-ray source 12' passes through an examination region 16', in this instance the stomach, of the examination object 17'. A parameter for recording the image, the x-ray source/detector distance 27', SID, was also set.

Figure 2:
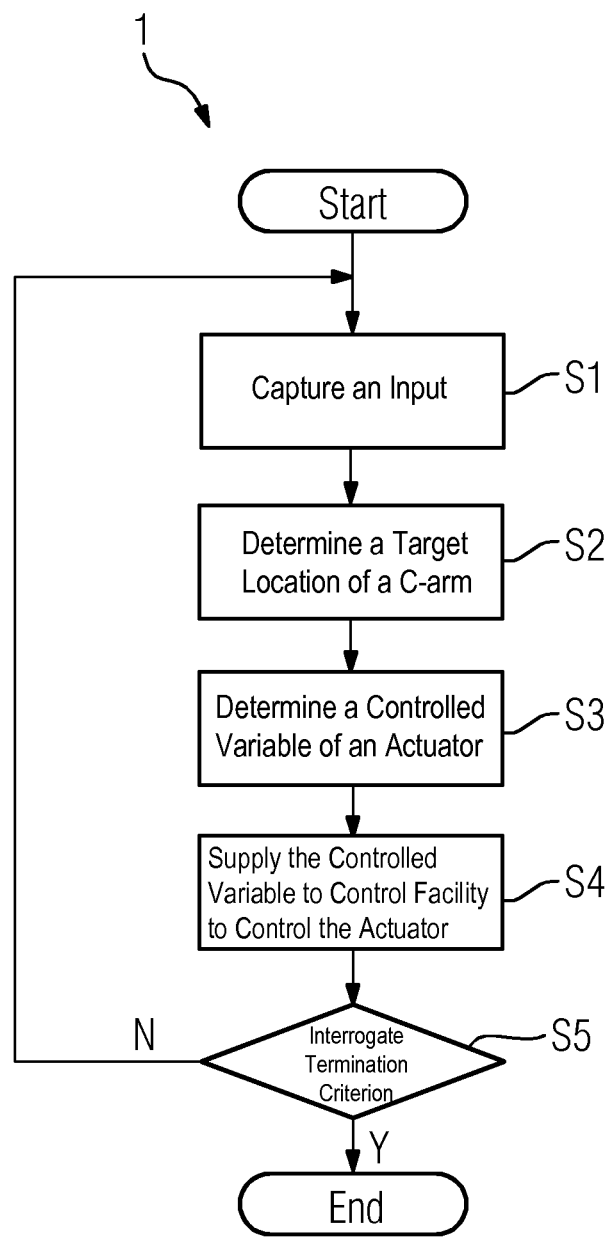
FIG. 2 shows a flow diagram of a disclosed method.

FIG. 2 shows by way of example a flow diagram of a disclosed method for controlling the movement of an x-ray apparatus. The method comprises the method steps S1 to S5, starts "Start" with method step S1 and ends "End" after method step S5. The individual method steps are as follows:
S1) Capturing an input at the operating unit of the operating facility;
S2) Determining a target location of the C-arm;
S3) Determining at least one controlled variable of the at least one actuator for positioning the C-arm;
S4) Supplying the at least one controlled variable to the control facility to control the at least one actuator;
S5) Interrogating a termination criterion.

If the termination criterion S5, such as the reaching of a predefinable number of method runs or the completion of a predefinable time period or the actuation of a button or the actuation of a switch, is met, "Y", the method is terminated. If the termination criterion is not met, "N", the method returns to method step S1.

Figure 3:
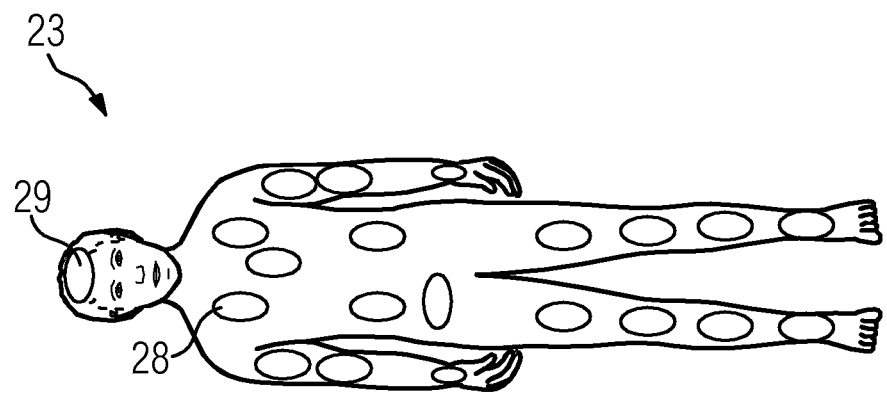
FIG. 3 shows an example of an image of an examination object.

FIG. 3 shows an example of an image 23 of an examination object. The image 23 represents a highly simplified plan view of a person. Marked in the anatomically correct position by ellipses are the location of organs and the location of body regions. The brain 29 and the right lung 28 are marked by way of example. Heart, upper arms, elbow, wrist, kidneys, abdomen with liver and body regions of the lower extremities are shown without reference characters.

Figure 4:
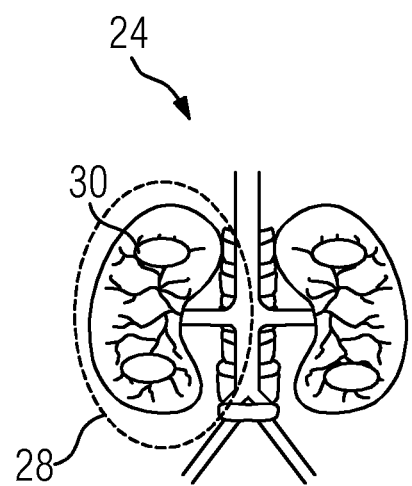
FIG. 4 shows an example of an image of a part of an examination object.

FIG. 4 shows an example of an image 24 of a part of an examination object. In this image the right lung 28 is shown differently. While in the representation in FIG. 3 virtually only the surface of the examination object is visible, FIG. 4 shows blood vessels and bone structures. It is conceivable that an operator, for example at a touch-sensitive screen, first selected the right lung 28 and then selected the upper part 30 of the lung 28 in the representation of the image 24.

Figure 5:
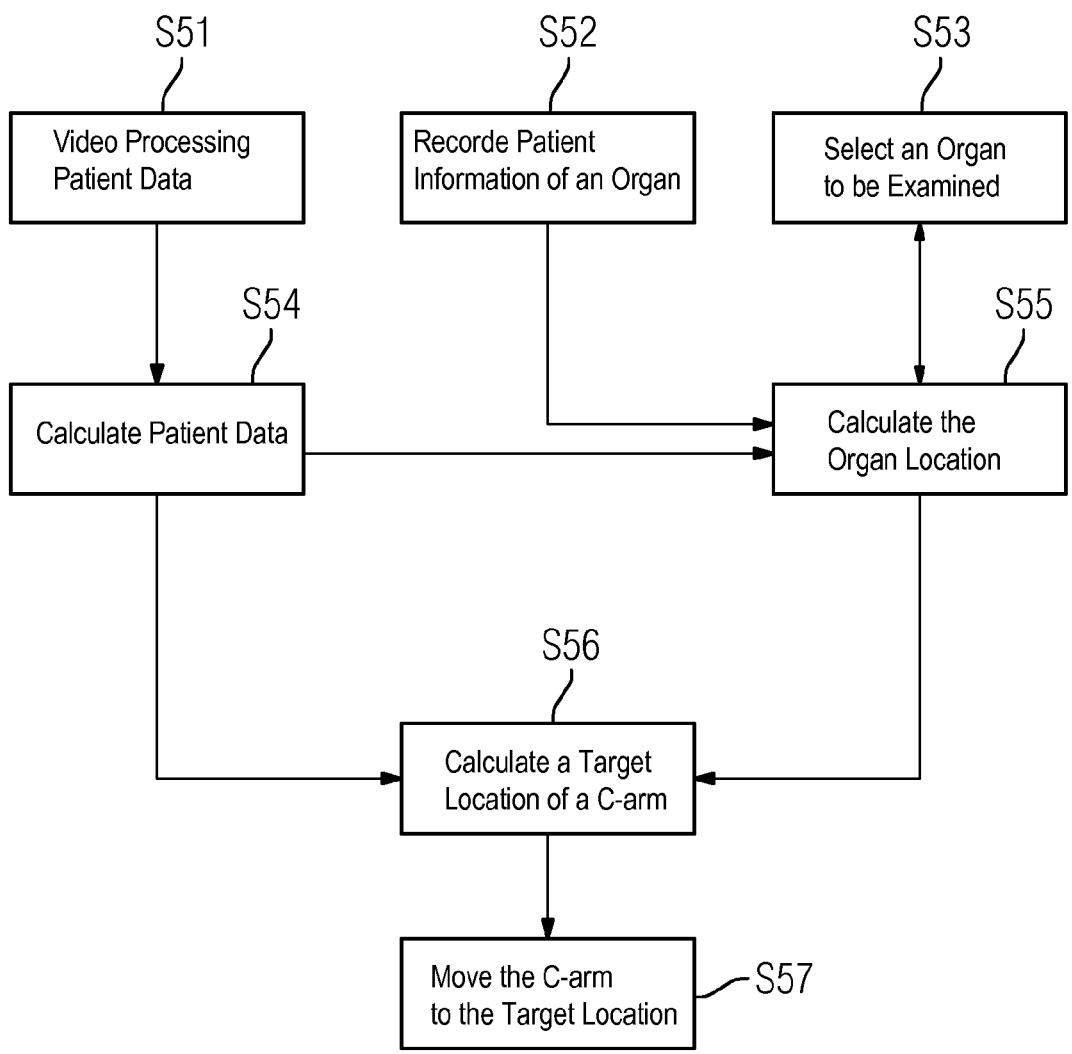
FIG. 5 shows a diagram to describe functional units of an example of a disclosed method.

FIG. 5 shows a diagram to describe possible functional units of an example of a disclosed method. Based on a standard patient, basic information relating to size and location of organs or a body region of a patient to be examined lying on a patient couch is recorded, S52. Video processing S51 allows further data about the patient, patient height, body shape and location of the patient on the patient couch, to be obtained and included in a patient data calculation S54. This patient data is included with the standard patient data in the calculation S55 of the location or organs and/or body regions. An operator selects, S53, on an image showing or representing at least one part of the patient to be examined, the organ or body region to be examined. The patient position and the location of the organ or body region to be examined are included in the calculation, S56, of a system position or target location of a C-arm. The system position to be assumed is transmitted, S57, to a movement controller, which moves the C-arm to the desired position.

Figure 6:
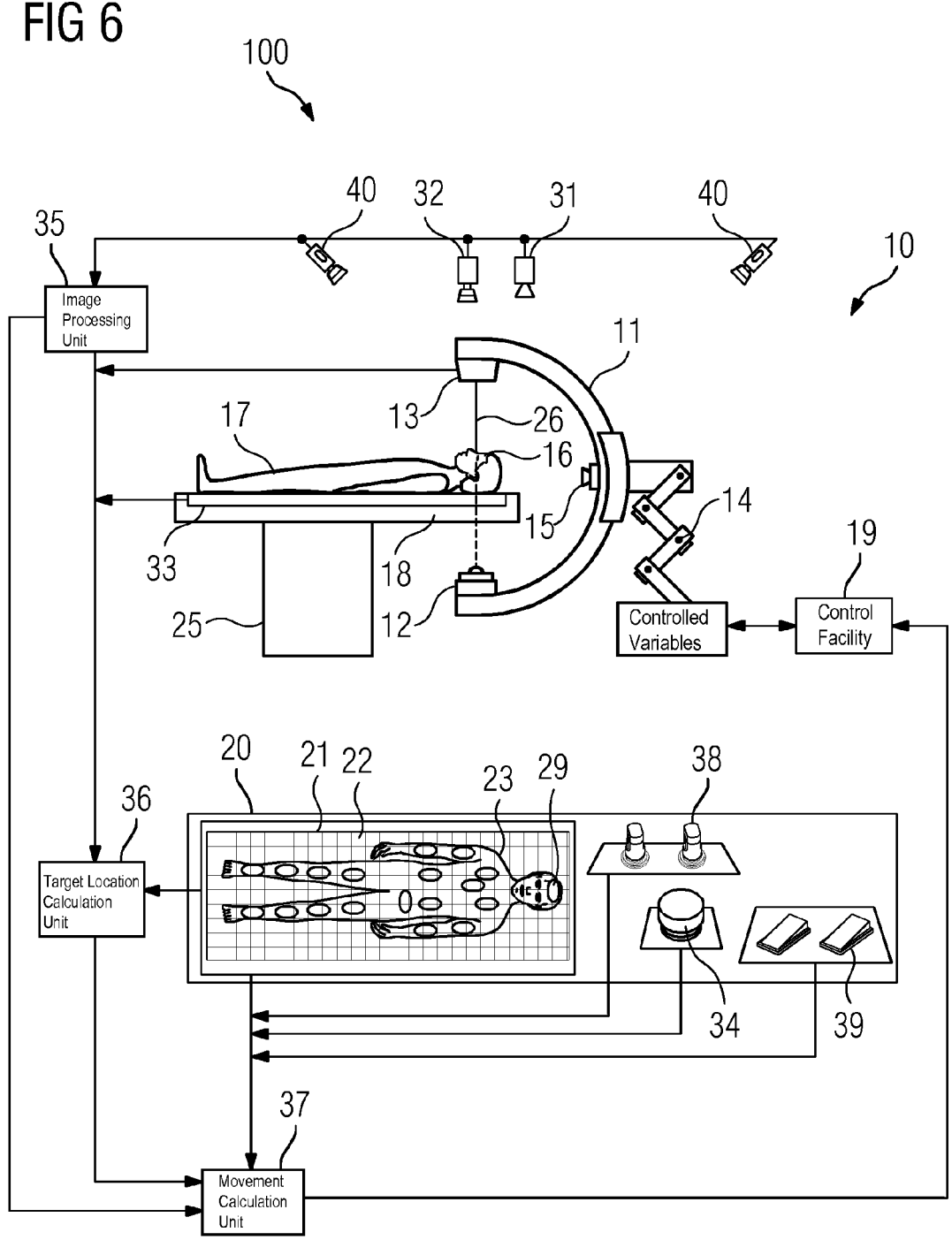
FIG. 6 shows a schematic representation of an embodiment of a disclosed x-ray system.

FIG. 6 finally shows a schematic representation of an embodiment of a disclosed x-ray system 100. An x-ray apparatus 10 has a C-arm 11, on which an x-ray source 12 and an x-ray detector 13 are disposed opposite one another. Lying on a support facility 18, e.g. an examination table, which is held in a movable manner by a column of the support facility 25, is an examination object 17, in this instance a human patient. The x-ray apparatus 10 is controlled by an operating facility 20, which comprises a number of operating unit, in this instance sensor elements 22 of a touch-sensitive screen 21, also referred to as a touch-screen, joysticks 38, foot switches 39 and a pushbutton 34, and a display apparatus, in this instance the touch-sensitive screen 21, and a control facility 19. The control facility 19 forwards inter alia controlled variables or control signals to actuators (the actuators 14 and 15 are shown by way of example) to the x-ray apparatus 10. The C-arm 11 of the x-ray apparatus 10 is disposed on a schematically illustrated, robot-like apparatus, which allows a number of degrees of freedom when positioning and aligning the C-arm 11 and thus the x-ray source 12 and x-ray detector 13. A target location of the C-arm 11, or of the x-ray source 12 and x-ray detector 13, is assumed in FIG. 6, so that the central beam 26 of the x-ray source 12 passes through an examination region 16, in this instance the head, of the examination object 17. The touch-sensitive screen displays an image 23 of the examination object 17, with the image 23 being supplemented by markings showing possible examination regions, e.g. also the head region 29, and also allows the selected examination region 29 to be input by direct touching of the image 23 or markings. It is thus possible to select points or even regions, e.g. by enlarging a detail. Once an examination region 29 has been selected, the selection is transmitted to a target location calculation unit 36. This target location calculation unit 36 receives further information from additional sensors. FIG. 6 shows a schematic diagram of different cameras. The camera 31 has image recorders that are sensitive in the infrared (IR) wavelength range and the camera 32 is embodied as a so-called time of flight camera (TOF), which can capture a matrix of distances in a measuring process by way of a transit time measurement. The two cameras 40 form a stereoscopic camera system, which can be used to generate a spatial image. The signals from one or more of these measuring instruments are supplied to an image processing unit 35 which, for example by an image processing or video processing algorithm, can perform a determination of the actual circumstances of the examination object, for example the actual size and/or the actual position of the examination object 17 on the support facility 18, as well as relating to other similarly moving objects. A pressure-sensitive measuring mat 33 integrated in the support facility 18, i.e. a mat with pressure-sensitive sensors, can be used, when a patient is positioned on it, to conclude the height, location, orientation and also the weight of the patient from the pattern of pressure measurement values. These values, like the data from the image processing unit 35, are transmitted to the target location calculation unit 36. The target location calculation unit 36 can take account of the data from the image processing unit 35, the sensor system 33 from the support facility 18, stored anatomical models and patient statistics or the location of organs and body regions of patients and the transmitted examination region selection to determine a target location for the C-arm. The target location determined by the target location calculation unit 36 and the data determined by the image processing unit 35 are supplied to a movement calculation unit 37. The movement calculation unit 37 comprises a path planner and a collision computer or a collision avoidance computer. The task of the path planner is to determine the kinematic position change of the C-arm from a first to a second, such as to the target location, position. The path planner here can take into account the mechanical structure of the x-ray apparatus 10 and known objects, such as non-moving objects, ceilings, columns or walls, and determine a time-optimized movement sequence. The task of the collision computer is to use object coordinates and their extension, which are supplied by the image processing unit 35, to prevent a collision of the C-arm and other components of the x-ray apparatus 10, by forwarding the obstacles to the path planner for a new calculation of the movement sequence or first slowing the movement and if necessary even stopping it. Further input variables for the movement calculation unit 37 can be the output variables of the operating unit of the operating facility 20. The joysticks 38 or foot switches 39 can be used for example to intervene in the movement sequence; such as after first traveling automatically, the C-arm 11 can be moved manually to a final target position. The pushbutton 34 could be used to terminate an automatically performed movement. The signals from the determined movement sequence are routed by the movement calculation unit 37 to the control facility 19, which activates the actuators 14 and 15 for example, so that the C-arm 11 moves to the intended target location.

Some aspects of the application and its embodiments are described as a summary. Operation by controlling individual directions and spatial angles by operating elements such as joysticks for example is replaced by organ or body region selection. The operator, for example a physician or a medical assistant, uses a touch-sensitive monitor or touch panel or displays to select a region to be displayed, e.g. left kidney, right knee, heart, by computer mouse control for example on an anatomical image. In some instances selection can take place in several stages in highly detailed regions, in other words when the abdomen is selected, a second, more detailed anatomical image of the abdomen showing the organs is displayed and the detailed selection only takes place at this second level. Region or organ preselection can also be narrowed down by a standard technical selection of a function group, e.g. "cardio" or "neuro", etc. Once this selection has been made it is conceivable for the operator to initiate travel of the C-arm system to the target region selected by anatomical selection using a safety-oriented operating element, e.g. a foot switch or joystick with DMG. In this process movements combined from six degrees of freedom can also be executed, which allows the examination region or region of interest, ROI, to be reached more quickly. The calculation of the path to be traveled takes place in a control facility, e.g. by way of a path planner, so that the operator does not have to worry about the individual movements required to reach the target location. A collision with a patient couch and other spatial elements can be avoided by way of a collision monitoring system correlated with the path planner, which can be integrated in the control facility. Once the target position is reached, the operator can use fluoroscopy to fine-tune the angle of the image using "standard" operating elements. Normally, in other words without further sensors, an anatomically standard patient is assumed to be in a standard position on the patient couch. Based on this basic data, the selection made by the operator and the anatomical representation stored in the system, i.e. of the standard patient, can then be used to calculate the position to be assumed in the system coordinate system and transmit it to the path planner, the collision avoidance system and finally to the motion or movement controller. This position can then be assumed after release by the operator. Further optimization of the method can be achieved by using additional sensors. The possibly relatively imprecise determination of the target location of the examination region, which is a function of patient positioning and size, can be optimized by capturing the actual patient using sensors. To this end video-based scans, e.g. time of flight cameras, can be used or for example tactile elements in the table, known as pressure mats. With knowledge of the positions and dimensions of the patient it is possible to determine the anatomy in general and also the position of the organ or region selected in the anatomical image specifically more precisely, allowing more precise travel to it. Position optimization can likewise be effected by evaluating the first available x-ray-fluoroscopy or recording images of the actual patient. To this end anatomical features can be extracted from the x-ray images and used to optimize the representation of the patient in the anatomical image in respect of size, dimensions and location of the organs. In one favorable instance a video-based sensor system for example can send information about spatial objects to the collision computer and path planner to increase the freedom from collision of the path to be traveled. Similarly the precise spatial orientation of imaging during travel as selected by the operator can be assigned either permanently to each organ or can take place by selection for the operator after selection by the latter of the organ/region.

Some significant feature of the application and its embodiments can be described as follows:
Simplified operation by focusing on the examination region, i.e. an organ or body region;
Joysticks are only used for fine-tuning or precise setting of the imaging angle or to confirm safety-oriented activation;
Shortened learning curve for operation of the x-ray apparatus;
Workflow optimization and shortening of operating and treatment time;
Greater efficiency and increased operator satisfaction;
Reduced risk of collision;
Dose reduction due to more efficient approximate adjustment of the system without fluoroscopy and storage of the anatomical structure of a standard patient.

The invention claimed is:

1. A method for controlling a movement of an x-ray apparatus having a C-arm comprising an x-ray source and an x-ray detector disposed opposite one another, comprising:
supporting an examination object on a support facility;
positioning the C-arm relative to an examination region of the examination object by an actuator;
controlling the x-ray source, the x-ray detector and the actuator by a control facility;
displaying an image representing an outline of a part of the examination object by a display apparatus of an operating facility;
selecting an input on the displayed image at an operating unit of the operating facility;
determining a target location of the C-arm as a function of the input, wherein the target location comprises a target position and a target alignment of the C-arm;
determining a controlled variable of the actuator and supplying the determined controlled variable to the control facility; and
controlling the actuator by the control facility based on the determined controlled variable,
wherein the image represents a simple outline of the examination object viewed from above,
wherein a location of an organ and/or a body region of the examination object is marked anatomically by a marking in the image,
wherein the target location of the C-arm is determined taken into account measurement data of the examination object using a measuring unit,
wherein the measuring unit comprises a pressure-sensitive sensor integrated in the support facility,
wherein the measuring unit further comprises at least one camera,
wherein the measuring unit measures the measurement data of the examination object comprising a height, a location, an orientation, and a weight of the examination object when the examination object is positioned on the support facility,
wherein the measurement data of the examination object from the pressure-sensitive sensor and from the at least one camera are combined for determining the target location of the C-arm,
wherein the target location of the C-arm is determined further taken into account a statistic from a number of examination objects, and
wherein the statistic comprises location of the part of the examination object relative to a size of the examination object.

2. The method as claimed in claim 1, wherein the target location of the C-arm is determined based on the image.

3. The method as claimed in claim 1, wherein the marking can be selected by the operating unit.

4. The method as claimed in claim 1, wherein the target location of the C-arm is determined further according to a standard position of the examination region relative to the support facility, and/or information from a medical file of the examination object.

5. The method as claimed in claim 1, wherein the measuring unit further comprises a unit selected from the group consisting of: a camera in a visible wavelength range, an IR camera, a time of flight camera, a laser scanner, an inductive measuring effect measuring unit, a capacitive measuring effect measuring unit, a heat radiation detection measuring unit, and a near field antenna measuring unit.

6. The method as claimed in claim 1, wherein the image is recorded using the x-ray apparatus.

7. The method as claimed in claim 1, wherein a detail of the image is enlarged and/or another representation from a different hierarchy of the image is displayed after the operating unit inputs the input.

8. The method as claimed in claim 1, wherein the operating facility comprises a touch-sensitive screen and/or a screen with an input unit.

9. The method as claimed in claim 8, wherein the input unit comprises a computer mouse.

10. The method as claimed in claim 1, wherein the controlled variable is determined according to an optimization algorithm.

11. The method as claimed in claim 10, wherein the optimization algorithm comprises a minimization of positioning time of the C-arm.

12. The method as claimed in claim 1, wherein the controlled variable is determined according to a collision avoidance algorithm.

13. The method as claimed in claim 12, wherein the collision avoidance algorithm considers a location of the operating facility, a location of the support facility, and a location of the examination object.

14. The method as claimed in claim 1, wherein a parameter for recording the image is determined as a function of the input.

15. The method as claimed in claim 14, wherein the parameter comprises an exposure time, an image repetition rate, a beam intensity, an x-ray source-detector distance, and/or a collimator setting.

16. The method as claimed in claim 1, wherein a sequence of target locations of the C-arm and/or a sequence of parameter settings for recording the image is determined as a function of the input.

17. The method as claimed in claim 1, wherein the method is executed repeatedly until a termination criterion is met, and wherein the termination criterion comprises reaching a predefinable number of method runs or a completion of a predefinable time period or an actuation of a button or an actuation of a switch.

18. The method as claimed in claim 1, wherein the method is executed automatically.

19. An x-ray system comprising an x-ray apparatus, comprising:
- a C-arm comprising an x-ray source and an x-ray detector disposed opposite one another;
- a support facility for supporting an examination object;
- an actuator for positioning the C-arm relative to an examination region of the examination object;
- a control facility for controlling the x-ray source, the x-ray detector and the actuator; and
- an operating facility comprising a display apparatus and an operating unit, wherein the display apparatus displays an image representing an outline of a part of the examination object, wherein an operator selects an input on the displayed image at an operating unit of the operating facility, wherein the operating facility determines a target location of the C-arm as a function of the input, wherein the operating facility determines a controlled variable of the actuator and supplies the determined controlled variable to the control facility, wherein the control facility controls the actuator based on the determined controlled variable, wherein the target location comprises a target position and a target alignment of the C-arm, wherein the image represents a simple outline of the examination object viewed from above, wherein a location of an organ and/or a body region of the examination object is marked anatomically by a marking in the image, wherein the target location of the C-arm is determined taken into account measurement data of the examination object using a measuring unit, wherein the measuring unit comprises a pressure-sensitive sensor integrated in the support facility, wherein the measuring unit further comprises at least one camera, wherein the measuring unit measures the measurement data of the examination object comprising a height, a location, an orientation, and a weight of the examination object when the examination object is positioned on the support facility, wherein the measurement data of the examination object from the pressure-sensitive sensor and from the at least one camera are combined for determining the target location of the C-arm, wherein the target location of the C-arm is determined further taken into account a statistic from a number of examination objects, and wherein the statistic comprises location of the part of the examination object relative to a size of the examination object.

* * * * *